US009295517B2

(12) United States Patent
Peyman et al.

(10) Patent No.: US 9,295,517 B2
(45) Date of Patent: *Mar. 29, 2016

(54) SYSTEM AND METHOD FOR GENERATING HEAT AT TARGET AREA OF PATIENT'S BODY

(71) Applicants: Nazmi Peyman, Richmond, VA (US); Kayvan Najarian, Northville, MI (US); Dennis James Rivet, II, Richmond, VA (US); John Frederick Reavey Cantwell, Richmond, VA (US)

(72) Inventors: Nazmi Peyman, Richmond, VA (US); Kayvan Najarian, Northville, MI (US); Dennis James Rivet, II, Richmond, VA (US); John Frederick Reavey Cantwell, Richmond, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/606,508

(22) Filed: Jan. 27, 2015

(65) Prior Publication Data
US 2015/0157404 A1    Jun. 11, 2015

(51) Int. Cl.
| A61B 18/18 | (2006.01) |
| A61N 1/40 | (2006.01) |
| A61N 7/02 | (2006.01) |
| A61B 18/00 | (2006.01) |
| A61N 5/02 | (2006.01) |
| A61N 7/00 | (2006.01) |

(52) U.S. Cl.
CPC .............. *A61B 18/18* (2013.01); *A61N 1/406* (2013.01); *A61N 7/02* (2013.01); *A61B 2018/00434* (2013.01); *A61B 2018/00791* (2013.01); *A61N 5/025* (2013.01); *A61N 2007/0021* (2013.01)

(58) Field of Classification Search
CPC .................. A61B 18/18; A61B 2018/00791; A61N 1/406; A61N 5/025
See application file for complete search history.

(56) References Cited

U.S. PATENT DOCUMENTS

| 2011/0224665 A1* | 9/2011 | Crosby et al. ................... 606/33 |
| 2013/0274735 A1* | 10/2013 | Hastings et al. ................ 606/34 |

* cited by examiner

*Primary Examiner* — Joseph Stoklosa
*Assistant Examiner* — Amanda Zink
(74) *Attorney, Agent, or Firm* — Barry Choobin; Patent 360 LLC

(57) ABSTRACT

A method and system is provided for generating and distributing heat at a target area of a patient's body for treating lesions, tumors, cancers, body pain and nerve pain. The generated heat and the tissue temperature are monitored in real time. The system comprises a radio frequency (RF) antenna for receiving the RF waves generated from the RF generator. A RF absorber comprising several closed loop circuits and a miniaturized thermometer are implanted inside the body close to the target tissue. A controller/optimizer regulates a frequency and a transmission timing of the RF waves based on the measured target tissue temperature. The thermometer, the RF absorber and the wireless transmitter are placed in a screw. The RF absorber is made of metal with RF absorption rate higher than that of biological tissues. A ultrasound energy is also used to treat the target area.

20 Claims, 11 Drawing Sheets

SYSTEM AND METHOD FOR GENERATING HEAT AT TARGET AREA OF PATIENT'S BODY

CROSS-REFERENCE TO RELATED APPLICATIONS

The present application claims the benefit and the priority of the U.S. Provisional Patent Application with Ser. No. 61/908,862 tiled on Nov. 26, 2013 and the U.S. Non-Provisional patent application Ser. No. 14/269,451, now U.S. Pat No. 8,986,296, filed on May 5, 2014. The present application is a continuation application of the U.S. Non-Provisional patent application with Ser. No. 14/269,451,now U.S. Pat. No. 8,986,296, filed on May 5, 2014. The contents of the above mentioned applications are incorporated in entirety by reference herein.

BACKGROUND

1. Technical Field

The embodiments herein generally relates to the medical systems and methods. The embodiments herein particularly relates to the treatment of lesions, tumors, cancer cells, body pain and nerve pain. The embodiments herein more particularly relates to a method and system for generating heat at a target area in a patient's body to treat the lesions, tumors, cancer cells, body pain and nerve pain.

2. Description of the Related Art

Heat has been used to manage pain since ancient days. In modern pain management, among other modalities, heat is used to cure lesions and to burn or change the behavior of nerves. Radio frequency therapy and other ablative procedures are typically adapted to treat various chronic pain cases. The radio frequency waves are employed to generate heat at the tip of a needle or probe and the heat generated is utilized to destroy a target. The target can be a nerve or an invasive tumor and a variety of growths. The process for generating heat using radio frequency waves involves steps of detecting the target area using X-rays or other surface landmarks; inserting the needle or probe through the skin and guiding the needle or probe to the target using X-rays or surface landmarks. Using radiofrequency waves or direct heat, the nerve or the target structure is burnt and destroyed. Further enough heat is generated to calm and cease pain. However nerves do grow back and typically the procedure needs to be repeated in six months to a year. This is due to the fact that the nerves that are ablated do grow back and in most cases, the pain of the patient returns. In the view of the foregoing, there is a need for a treatment method for repeatedly providing heat to the target are at short or long term intervals.

In order to access the target, the physician needs to insert a needle or probe through the skin at each session. The needle has to go through many layers of tissue including skin, connective tissue and muscles. This increases the chance for complications including infections and bleeding. The needle itself causes pain as well. The ultimate position of the needle also varies to some degree at each procedure. Hence there is a need for eliminating the need for inserting the needles and probes into the body of the patient at periodic intervals such as every few months and reducing a pain of the patient and discomfort from the repeated insertion of the needles. Also, there is a need for a treatment method that reduces the risks of infection and bleeding and reduces cost.

MRI magnets are known to produce a significant amount of heat in the metal objects in the magnetic field. But the drawback of using MRI magnets is exhibited, when certain types of metal implants cause harmful effects in patients, for example, the ones used in pacemaker devices, by generating an uncontrolled amount of heat and tissue damage. Further there is a need for providing a facility for monitoring and reporting temperature at the target area to the physician remotely.

Hence there is a need for eliminating the need for inserting the needles and probes into the body of the patient at periodic intervals thereby reducing a pain of the patient and discomfort from the repeated insertion of the needles. Also, there is a need for a treatment method that reduces the risks of infection and bleeding and reduces cost. Further there is a need for providing a system and method for monitoring and reporting temperature at the target area to the physician remotely. Still further there is a need for a system with and without a battery for generating heat at a target area of a patient's body to irradiate and destroy tumor/tumors with optimized magnitude and timing of the RF energy. Yet there is a need to develop a system and method to generate and deliver different amounts of RF energies or ultrasound energies to different target areas in a patient body to irradiate only a tissue that requires treatment thereby eliminating an over irradiation of all other tissues.

The above mentioned shortcomings, disadvantages and problems are addressed herein and which will be understood by reading and studying the following specification.

Objects of the Embodiments

The primary object of the embodiments herein is to provide a system and method for generating heat at a target area of a body of a patient to treat the lesions, tumors, cancer cells, body pain and nerve pain.

Another object of the embodiments herein is to provide a treatment method for repeatedly generating heat to the target area at short or long intervals of time.

Yet another object of the embodiments herein is to provide a temperature monitor and control system for remotely observing and notifying a temperature condition at the target area.

Yet another object of the embodiments herein is to provide a tissue friendly apparatus manufactured from the metals/alloys that maximize a heat generation.

Yet another object of the embodiments herein is to implant the needles/probes at the target location of patient's body in-order to eliminate a need to insert the needle/probe on multiple occasions.

Yet another object of the embodiments herein is to implant a battery inside a body of the patient to supply electrical power to the implanted temperature sensor and wireless transmitter.

Yet another object of the embodiments herein is to employ a ultrasonic generator or transducer to generate energy for producing a lesion or heat to induce analgesia in the target area of the patient's body.

These and other objects and advantages of the present invention will become readily apparent from the following detailed description taken in conjunction with the accompanying drawings.

SUMMARY

The various embodiments herein provide a method and for generating heat at a target area of a patient's body. The system uses radio frequency radiation to generate heat inside a tissue of the target and the heat generated is distributed throughout the target area.

According to one embodiment herein, a system is provided for generating heat at a target area of a patient's body. The system comprises a radio frequency (RF) generator for generating radio frequency (RF) waves and a radio frequency (RF) antenna or transducer for receiving the generated radio frequency (RF) waves from the radio frequency (RF) generator. A controller or optimizer is provided for controlling a frequency of the radio frequency (RF) waves and a transmission timing which comprises a start time and a stop time of the transmission of the radio frequency (RF) waves. A radio frequency (RF) absorber or distributor comprising a plurality of closed loop circuits is provided. A miniaturized thermometer is arranged for measuring the temperature and transmitting the measured temperature value to a wireless transmitter. The wireless transmitter further transmits the measured temperature value to a wireless receiver.

According to one embodiment herein, the miniaturized thermometer is positioned inside the radio frequency absorber or distributor. The miniaturized thermometer is adapted to be positioned close to the target area of the patient's body.

According to one embodiment herein, the miniaturized thermometer is positioned close to the nerve or the disk to be irradiated.

According to one embodiment herein, the miniaturized thermometer is a temperature sensor.

According to one embodiment herein, the radio frequency (RF) antenna or transducer, the controller or optimizer and the wireless receiver collectively form an external part of the system.

According to one embodiment herein, the miniaturized thermometer, the radio frequency (RF) absorber or distributor and the wireless transmitter collectively form an internal part of the system.

According to one embodiment herein, the miniaturized thermometer, the radio frequency (RF) absorber or distributor and the wireless transmitter are placed in a screw. The screw is made of metals with a high radio frequency (RF) absorption characteristics or coefficient. The radio frequency (RF) absorber or distributor is made of metal or silicon based material whose rate of absorbing radio frequency (RF) is higher than that of biological tissues.

According to one embodiment herein, the wireless transmitter is configured to transmit the measured temperature value acquired from the miniaturized thermometer to the wireless receiver. The wireless receiver is placed outside the body of the patient.

According to one embodiment herein, the wireless receiver is configured to transmit the received temperature value to the controller or optimizer.

According to one embodiment herein, the controller or optimizer calculates a preferred value for RF energy, RF frequency, start and stop time for the treatment, and wherein the values are calculated based on the received temperature value.

According to one embodiment herein, the controller or optimizer is selected from a group consisting of a Proportional-Integral-Derivative (PID) controller, an Optimal Controller, a Fuzzy Controller, a Neural Controller and a Model-Based Controller.

According to one embodiment herein, the controller or optimizer is further configured to maintain the level of measured temperature inside the tissue at a desired level during a course of treatment.

According to one embodiment herein, the radio frequency (RF) antenna or transducer is configured to receive the RF energy value, RF frequency value, and start and stop time for the treatment. The radio frequency (RF) generator is configured to irradiate the RF energy towards the target area of the patient's body or nerve or disk and the radio frequency (RF) absorber or distributor.

According to one embodiment herein, the radio frequency (RF) absorber or distributor is provided for a re-circulation of radio frequency (RF) energy. The radio frequency (RF) absorber or distributor is configured to generate heat from the magnetic energy of radio frequency (RF). The radio frequency (RF) absorber or distributor is further configured to distribute the generated heat to the target area of the patient's body or nerve or the disk.

According to one embodiment herein, the screws or the absorbers or the distributors convert the magnetic energy to heat inside the tissue and transfer the heat to the target area of the patient's body or disks or nerves.

According to one embodiment herein, the target area of the patient's body is selected from a group consisting of disks, nerves, bones, and tumor tissues.

According to one embodiment herein, the system further comprises a battery implanted inside the patient's body to supply electrical power to the temperature sensor and the wireless transmitter.

According to one embodiment herein, the system further comprises an ultrasonic generator or ultrasonic transducer to generate energy for producing a lesion or heat to induce analgesia in the target area of the patient's body.

According to an embodiment herein, a method is provided for generating heat at a target area of a patient's body. The method comprises the steps of identifying a target area in a patient's body for radio-frequency ablation. On locating the target area, one or more wires or probes or plates or rods are inserted and implanted at the target area of the patient's body. Further an amount of radio frequency (RF) energy required to irradiate the target area in the patient's body to achieve the desired temperature at the target area is calculated. The patient is placed in a magnetic field of the generated RF waves. A heat is generated around the target area of the patient's body utilizing the generated radio frequency (RF) waves. The heat generated at the target area destroys the target area remotely.

According to one embodiment herein, the temperature at the target area is monitored remotely and the monitored temperature information is sent to the physician at regular intervals of time.

According to one embodiment herein, the method for generating heat at the target area of the patient's body further comprises the steps of calculating the amount of radio frequency energy required to achieve the desired temperature at the target area. The steps involves estimating the values of at-least last two measured temperatures at time "t-1" and "t" respectively. One or more fuzzy rules are applied on the estimated temperature values at time "t-1" and "t". The power of the radio frequency (RF) is identified based on the fuzzy rules and the temperature values. Further the frequency and timing of radio frequency (RF) is identified based on the measured temperature.

According to one embodiment herein, the identification of the target area in the patient's body for radiofrequency ablation is done through one or more imaging studies selected from a group consisting of X-rays, CT scans, MRIs, and physical examination of the patient, response to previous treatment modalities, and diagnostic local anesthetic injections. The probe is inserted when the target is identified.

According to one embodiment herein, the wire type probes are inserted percutaneously using a needle under the guidance of fluoroscopy or CT scan.

According to one embodiment herein, the larger probes and rods are inserted surgically under direct vision and secured at the target location in the patient's body.

According to one embodiment herein, the method provides a real time monitoring of the generated heat and the temperature of the tissue.

According to one embodiment herein, the target area of the patient's body is selected from a group consisting of disks, nerves, bones, and tumor tissues.

According to one embodiment herein, the method further comprises a real time monitoring of the heat generated and the temperature of the tissue.

According to one embodiment herein, the method further comprises implanting a battery inside the patient's body to supply an electrical power to the temperature sensor and the wireless transmitter.

According to one embodiment herein, the method further comprises employing or utilizing an ultrasonic generator or ultrasonic transducer to generate energy for producing a lesion or heat to induce analgesia in the target area of the patient's body.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
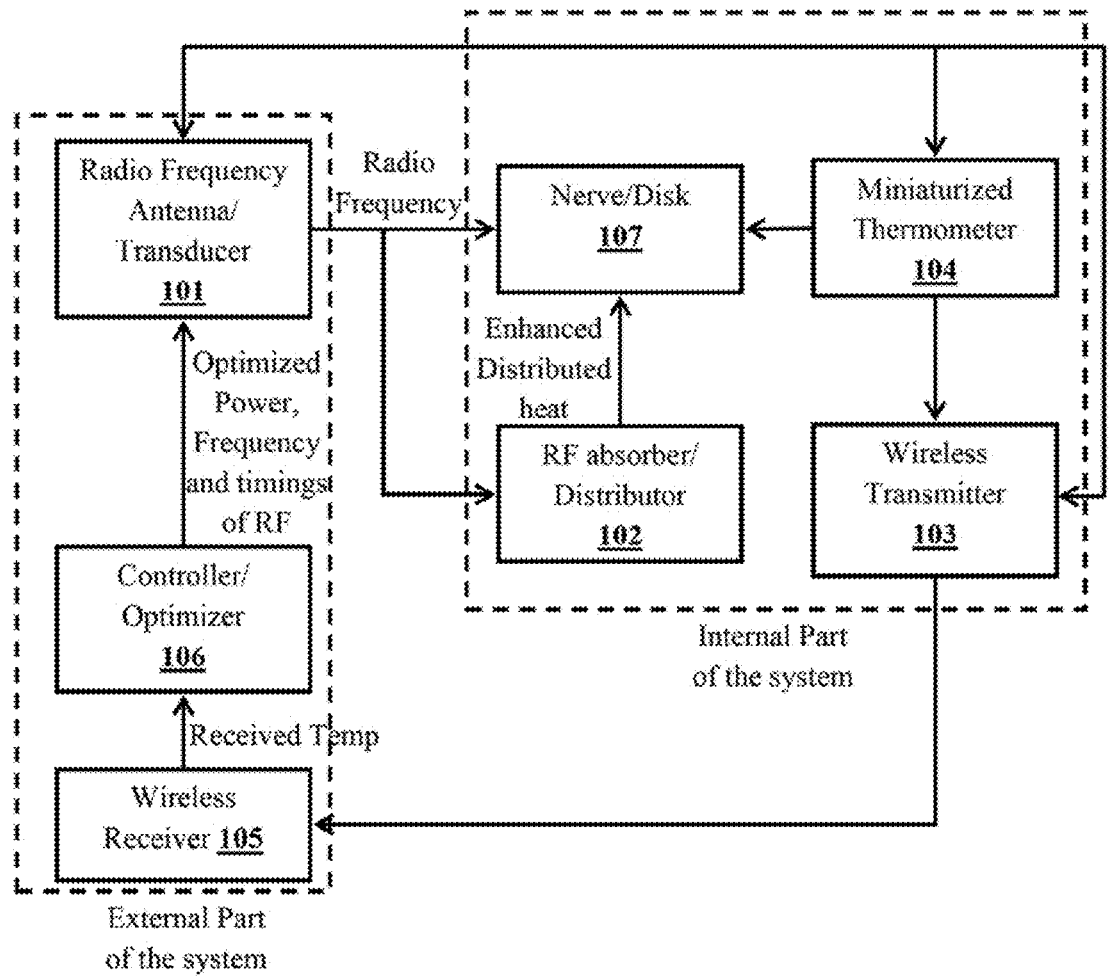
FIG. 1 illustrates a block diagram of the system for generating heat at the target area of the patient's body, according to an embodiment herein.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a method and for generating heat at a target area of a patient's body. The system uses radio frequency radiation to generate heat inside a tissue of the target and the heat generated is distributed throughout the target area.

According to one embodiment herein, a system is provided for generating heat at a target area of a patient's body. The system comprises a radio frequency (RF) generator for generating radio frequency (RF) waves and a radio frequency (RF) antenna or transducer for receiving the generated radio frequency (RF) waves from the radio frequency (RF) generator. A controller or optimizer is provided for controlling a frequency of the radio frequency (RF) waves and a transmission timing which comprises a start time and a stop time of the transmission of the radio frequency (RF) waves. A radio frequency (RF) absorber or distributor comprising a plurality of closed loop circuits is provided. A miniaturized thermometer is arranged for measuring the temperature and transmitting the measured temperature value to a wireless transmitter. The wireless transmitter further transmits the measured temperature value to a wireless receiver.

According to one embodiment herein, the miniaturized thermometer is positioned inside the radio frequency absorber or distributer. The miniaturized thermometer is adapted to be positioned close to the target area of the patient's body.

According to one embodiment herein, the miniaturized thermometer is positioned close to the nerve or the disk to be irradiated.

According to one embodiment herein, the miniaturized thermometer is a temperature sensor.

According to one embodiment herein, the radio frequency (RF) antenna or transducer, the controller or optimizer and the wireless receiver collectively form an external part of the system.

According to one embodiment herein, the miniaturized thermometer, the radio frequency (RF) absorber or distributor and the wireless transmitter collectively form an internal part of the system.

According to one embodiment herein, the miniaturized thermometer, the radio frequency (RF) absorber or distributor and the wireless transmitter are placed in a screw. The screw is made of metals with a high radio frequency (RF) absorption characteristics or coefficient. The radio frequency (RF) absorber or distributor is made of metal or silicon based material whose rate of absorbing radio frequency (RF) is higher than that of biological tissues.

According to one embodiment herein, the wireless transmitter is configured to transmit the measured temperature value acquired from the miniaturized thermometer to the wireless receiver. The wireless receiver is placed outside the body of the patient.

According to one embodiment herein, the wireless receiver is configured to transmit the received temperature value to the controller or optimizer.

According to one embodiment herein, the controller or optimizer calculates a preferred value for RF energy, RF frequency, start and stop time for the treatment, and wherein the values are calculated based on the received temperature value.

According to one embodiment herein, the controller or optimizer is selected from a group consisting of a Proportional-Integral-Derivative (PID) controller, an Optimal Controller, a Fuzzy Controller, a Neural Controller and a Model-Based Controller.

According to one embodiment herein, the controller or optimizer is further configured to maintain the level of measured temperature inside the tissue at a desired level during a course of treatment.

According to one embodiment herein, the radio frequency (RF) antenna or transducer is configured to receive the RF energy value, RF frequency value, and start and stop time for the treatment. The radio frequency (RF) generator is configured to irradiate the RF energy towards the target area of the patient's body or nerve or disk and the radio frequency (RF) absorber or distributor.

According to one embodiment herein, the radio frequency (RF) absorber or distributor is provided for a re-circulation of radio frequency (RF) energy. The radio frequency (RF) absorber or distributor is configured to generate heat from the magnetic energy of radio frequency (RF). The radio frequency (RF) absorber or distributor is further configured to distribute the generated heat to the target area of the patient's body or nerve or the disk.

According to one embodiment herein, the screws or the absorbers or the distributors convert the magnetic energy to heat inside the tissue and transfer the heat to the target area of the patient's body or disks or nerves.

According to one embodiment herein, the target area of the patient's body is selected from a group consisting of disks, nerves, bones, and tumor tissues.

According to one embodiment herein, the system further comprises a battery implanted inside the patient's body to supply electrical power to the temperature sensor and the wireless transmitter.

According to one embodiment herein, the system further comprises an ultrasonic generator or ultrasonic transducer to generate energy for producing a lesion or heat to induce analgesia in the target area of the patient's body.

According to an embodiment herein, a method is provided for generating heat at a target area of a patient's body. The method comprises the steps of identifying a target area in a patient's body for radio-frequency ablation. On locating the target area, one or more wires or probes or plates or rods are inserted and implanted at the target area of the patient's body. Further an amount of radio frequency (RF) energy required to irradiate the target area in the patient's body to achieve the desired temperature at the target area is calculated. The patient is placed in a magnetic field of the generated RF waves. A heat is generated around the target area of the patient's body utilizing the generated radio frequency (RF) waves. The heat generated at the target area destroys the target area remotely.

According to one embodiment herein, the temperature at the target area is monitored remotely and the monitored temperature information is sent to the physician at regular intervals of time.

According to one embodiment herein, the method for generating heat at the target area of the patient's body further comprises the steps of calculating the amount of radio frequency energy required to achieve the desired temperature at the target area. The steps involves estimating the values of at-least last two measured temperatures at time "t-1" and "t" respectively. One or more fuzzy rules are applied on the estimated temperature values at time "t-1" and "t". The power of the radio frequency (RF) is identified based on the fuzzy rules and the temperature values. Further the frequency and timing of radio frequency (RF) is identified based on the measured temperature.

According to one embodiment herein, the identification of the target area in the patient's body for radiofrequency ablation is done through one or more imaging studies selected from a group consisting of X-rays, CT scans, MRIs, and physical examination of the patient, response to previous treatment modalities, and diagnostic local anesthetic injections. The probe is inserted when the target is identified.

According to one embodiment herein, the wire type probes are inserted percutaneously using a needle under the guidance of fluoroscopy or CT scan.

According to one embodiment herein, the larger probes and rods are inserted surgically under direct vision and secured at the target location in the patient's body.

According to one embodiment herein, the method provides a real time monitoring of the generated heat and the temperature of the tissue.

According to one embodiment herein, the target area of the patient's body is selected from a group consisting of disks, nerves, bones, and tumor tissues.

According to one embodiment herein, the method further comprises a real time monitoring of the heat generated and the temperature of the tissue.

According to one embodiment herein, the method further comprises implanting a battery inside the patient's body to supply an electrical power to the temperature sensor and the wireless transmitter.

According to one embodiment herein, the method further comprises employing or utilizing an ultrasonic generator or ultrasonic transducer to generate energy for producing a lesion or heat to induce analgesia in the target area of the patient's body.

According to one embodiment herein, the system comprises a small battery implanted inside the body to supply the electrical power to energise both the implanted temperature sensor and wireless transmitter, thereby eliminating a need for recharging/powering-up of the temperature sensor and wireless transmitter using the externally irritated RF power.

According to one embodiment herein, the implanted battery is a rechargeable. The battery is recharged wirelessly.

According to one embodiment herein, the system is also customized to irradiate and destroy tumor/tumors with optimized magnitude and timing of the RF energy. Again, this process is implanted in two ways/modes with regards to the energy delivery mechanism that is used to power up the implanted components. In the first mode, a battery is implanted along with thermometer and wireless transmitter, while in the second mode, the external RF is used to charge the researchable thermometer and wireless transmitter that use the received RF to recharge/activate. In both the modes, the major portion of RF energy is absorbed by the RF absorber(s)/distributer(s) that are surgically positioned close/attached to the tumor, thereby ensuring that the RF energy transmitted from the absorber(s)/distributer(s) to the tumor is converted into heat, to damage the cancer/tumor cells. The thermometer is also positioned closely/attached to the tumor to measures the temperature during the procedure. The measured temperature is transmitted wirelessly to the controller positioned outside the patient body and is analyzed by the controller/optimizer so that the dose/timing of the energy during each treatment as well as planning of the following treatments are optimized based on the measurements.

The main and ultimate objective in the treatment of tumors with RF (in both pain management and tumor suppression) is the delivery of different amounts of RF energy to different parts of the tissue being irradiated. Since the irradiated tissues are mainly in contact or in close vicinity of the absorbers/distributers in the embodiments disclosed herein RF energies of different magnitudes are delivered to a plurality of absorbers/distributors implanted in the body of the patient so that the amount of RF energy delivered to the plurality absorbers/distributors is mutually different.

An affinity to absorb RF in different materials (e.g. metals/alloys) varies at different RF frequencies. In other words, Metal A has the maximum level of absorbance at frequency f1 while Metal 2 has a peak absorbance at f2, and Metal 3 at f3. In covering the pedicle screws and other instrumentation with absorbers/distributers, the embodiments herein discloses that the different parts of the instrumentations are covered with different absorber materials having significantly different maximum peak absorbance RF frequencies so that only the targeted absorbent and the tissue around the target are highly affected/irradiated by the RF energy during the irradiation of the absorbers of different materials with a specific RF energy or when the absorbers of different materials are exposed to a same RF wave of a specific frequency. As a result, the embodiments herein disclose a system and method for irradiating only the tissue that requires treatment at each treatment session and avoid over-irradiation of all other tissues.

The embodiments herein disclose a system that is used for both existing spinal hardware already implanted in patient's body as well as the new hardware to be implanted in patients. Specifically, According to an embodiment herein, a system is developed for use with the patients who are already provided with an existing hardware facility. The embodiments herein provide a new hardware component (absorbers, thermometer and wireless transmitter) along with the algorithmic/software components that is inserted/implanted as a free-standing/separate/stand-alone device through a simple surgical procedure in a clinic or hospital operating room, percutaneously or through a surgical incision.

According to an embodiment herein, a more recommended/efficient method of implementing the system is to integrate the hardware components (absorbers, thermometer and wireless transmitter) as a component of the spinal instrumentation that are implanted in the patient from the beginning. This integration the hardware components in the beginning not only avoids additional surgery but also creates a more effective standard of practice in the field for spinal instrumentation that allows intelligent and targeted RF treatment.

According to an embodiment herein, a free-standing device or a stand alone device/component and the form is made as a part of the hardware. According to an embodiment herein, the stand alone hardware device is also used for other non-spinal uses, for example hip and knee replacement hardware. The stand alone hardware device helps to reduce the pain experienced by the patients after implantation of the hardware and after the normal healing phase is lapsed.

According to an embodiment herein, the system and method provides a mechanism of action for treating a target area of the patient's body or tumor with RF energy or ultrasonic energy is as follows. The system and method of the embodiments herein produce analgesia via one or more of the following mechanisms amongst other mechanisms of action. At first the system and method produces heat. The RF energy or ultrasonic energy produces heat at the target area to destroy the nerves and other structures. Secondly, the system and method increases blood circulation to an area thereby increasing a supply of oxygen and nutrients and expedite in eliminating carbon dioxide and metabolic wastes from the target area. Thirdly, the system and method activates nociception locally to activate nervous system pathways and other non-nerve cells and pathways and tissues to produce analgesia. Thus the system and method of the embodiments herein provide the three different mechanisms of action that are achieved and regulated by controlling the energy delivered to the target area and the temperature achieved at the target area and the length of the procedure.

According to an embodiment herein, ultrasound is also used in addition to or in place of Radio frequency (RF) to generate energy for the purpose of producing a lesion or heat to induce analgesia using the same methods and system disclosed in the embodiments herein.

The various embodiments herein provide a method and system generating heat at a target area of a patient's body. The system for generating heat at a target area of a patient's body comprises a radio frequency (RF) generator for generating radio frequency (RF) waves and a radio frequency (RF) antenna or transducer for receiving the generated radio frequency (RF) waves from the radio frequency (RF) generator. A controller or optimizer is provided for controlling a frequency of the radio frequency (RF) waves and a transmission timing which comprises a start time and a stop time of the transmission of the radio frequency (RF) waves. A radio frequency (RF) absorber or distributor comprising a plurality of closed loop circuits is provided. A miniaturized thermometer is arranged for measuring the temperature and transmitting the measured temperature to a wireless transmitter. The wireless transmitter further transmits the measured temperature to a wireless receiver.

According to one embodiment herein, the miniaturized thermometer is positioned inside the radio frequency absorber or distributer. The miniaturized thermometer is positioned close to the nerve or the disk to be irradiated.

According to one embodiment herein, the radio frequency (RF) antenna or transducer, the controller or optimizer and the wireless receiver collectively form an external part of the system.

According to one embodiment herein, the miniaturized thermometer, the radio frequency (RF) absorber or distributor and the wireless transmitter collectively form an internal part of the system.

According to one embodiment herein, the miniaturized thermometer, the radio frequency (RF) absorber or distributor and the wireless transmitter are placed in a screw. The screw is made of metals with a high radio frequency (RF) absorption characteristics or coefficient. The radio frequency (RF) absorber or distributor is made of metal or silicon based material whose rate of absorbing radio frequency (RF) is higher than that of biological tissues.

According to one embodiment herein, the wireless transmitter is configured to transmit the measured temperature with the miniaturized thermometer to the wireless receiver. The wireless receiver is placed outside the body of the patient.

According to one embodiment herein, the wireless receiver is configured to transmit the received temperature information to the controller or optimizer.

According to one embodiment herein, the controller or optimizer calculates a preferred value for RF energy, RF frequency, start and stop time for the treatment, and wherein the values are calculated based on the received temperature information.

According to one embodiment herein, the controller or optimizer is selected from the group consisting of a Proportional-Integral-Derivative (PID) controller, an Optimal Controller, a Fuzzy Controller, a Neural Controller and a Model-Based Controller.

According to one embodiment herein, the controller or optimizer is further configured to maintain the level of measured temperature inside the tissue at a desired level during the course of treatment.

According to one embodiment herein, the radio frequency (RF) antenna or transducer is configured to receive the RF energy value, RF frequency value, and start and stop time for the treatment. The radio frequency (RF) generator is configured to irradiate the RF energy towards the nerve or disk and the radio frequency (RF) absorber or distributor.

According to one embodiment herein, the radio frequency (RF) absorber or distributor provides for a re-circulation of radio frequency (RF) energy. The radio frequency (RF) absorber or distributor is configured to generate heat from the magnetic energy of radio frequency (RF). The radio frequency (RF) absorber or distributor is further configured to distribute the generated heat to the nerve or the disk.

According to one embodiment herein, the screws or the absorbers or the distributors convert the magnetic energy to heat inside the tissue and transfer the heat to disks and nerves.

The various embodiments herein provide a method for generating heat at a target area of a patient's body. The method comprises the steps of identifying a target area in a patient's body for radio-frequency ablation. On locating the target area, one or more wires or probes or plates or rods are inserted and implanted at the target area of the patient's body. Further the amount of radio frequency (RF) energy required to achieve the desired temperature at the target site is calculated. The patient is placed in a magnetic field of the generated RF waves. The heat is generated around the target area of the patient's body utilizing the radio frequency (RF) waves. The heat generated destroys the target remotely.

According to one embodiment herein, the temperature at the target area is monitored remotely and the monitored temperature information is sent to the physician at regular interval of time.

According to one embodiment herein, the identification of the target area in the patient's body for radiofrequency ablation is done through one or more imaging studies selected from the group consisting of X-rays, CT scans, MRIs, and physical examination of the patient, response to previous treatment modalities, and diagnostic local anesthetic injections, and wherein the probe is inserted when the target is identified.

According to one embodiment herein, the wire type probes are inserted percutaneously using a needle under the guidance of fluoroscopy or CT scan.

According to one embodiment herein, the larger probes and rods are inserted surgically under direct vision and secured at the target location in the patient's body.

According to one embodiment herein, the method for generating heat at the target area of the patient's body further comprises the steps of calculating the amount of radio frequency energy required to achieve the desired temperature at the target site. The steps involves an estimation of values of at-least last two measured temperatures at time "t-1" and "t". One or more fuzzy rules are applied on the estimated temperature values at time "t-1" and "t". The power of the radio frequency (RF) is identified based on the fuzzy rules and the temperature values. Further the frequency and timing of radio frequency (RF) is identified based on the measured temperature.

According to one embodiment herein, the method provides a real time monitoring of the generated heat and the temperature of the tissue.

The various embodiments herein provide a method and system for generating heat at a target area of a patient's body. The system uses radio frequency radiation to generate heat inside a tissue of the target and the heat generated is distributed throughout the target area. FIG. 1 illustrates a block diagram of a system that generates heat at the target area of the patient's body, according to an embodiment herein. The system comprises an internal part/unit/section and an external part/unit/section. The system comprises a plurality of needles/probes/plates/rods, a radio frequency (RF) antenna/transducer 101, a radio frequency (RF) generator, a controller/optimizer 106, a wireless receiver 105, a radio frequency (RF) absorber/distributor 102, a miniaturized thermometer 104, and a wireless transmitter 103. The miniaturized thermometer 104, the radio frequency (RF) absorber/distributor 102, the wireless transmitter 103 and the plurality of needles/probes collectively or integrally form an internal part/unit of the system. The radio frequency (RF) antenna/transducer 101, the controller/optimizer 106 and the wireless receiver 105 collectively form an external part/unit of the system. The internal part/unit of the system is implanted at the target location of the patient's body. The external part/unit of the system is placed outside the patient's body and is under supervision of a physician.

According to one embodiment herein, the system comprises the plurality of needles/probes/plates/rods which are inserted and implanted at the target area in the patient's body. The implanting of needle/probe at the target location eliminates the need to re-insert the needle/probe for plurality of times or several times thereby potentially decreasing the risk of infection, bleeding and the discomfort from the insertion of the needle. The radio frequency radiation generates heat at the tip of a needle or probe. The target area for radio-frequency ablation is typically identified using a decision making process that includes imaging studies, like X-rays, CT scans and MRIs, physical examination of the patient, response to previous treatment modalities, and diagnostic local anesthetic injections, in-order to confirm that the target is actually involved in a pain generating process. Once the target is identified, the wire type probes are inserted percutaneously using a needle under the guidance of fluoroscopy or CT scan. The larger probes and rods are placed surgically under direct vision and secured at the target location.

According to one embodiment herein, the miniaturized thermometer 104 of the system is configured to measure a temperature of a nerve or disk 107 at the target place. The miniaturized thermometer 104 is positioned inside the RF absorber/distributor 102, and the absorber/distributor 102 is placed close to the nerve or disk 107 to be irradiated. The information corresponding to the measured temperature is transmitted over the wireless transmitter 103 to the external part of the system. The miniaturized thermometer 104 and the wireless transmitter 103 operates on a radio frequency (RF) charged battery. The battery uses the RF energy emitted by the RF transducer to recharge itself.

According to one embodiment herein, the external part of the system receives the measured temperature information through the wireless receiver 105. The controller/optimizer 106, in communication with the wireless receiver 105, is configured to calculate a suitable value for RF energy and frequency as well as the start/stop time for the treatment. The values are calculated based on the received temperature information. The controller/optimizer 106 is selected from the group consisting of a variety of controllers including but not restricted to a Proportional-Integral-Derivative (PID) controller, an Optimal Controller, a Fuzzy Controller, a Neural Controller, a Model-Based Controller and the like. The control criterion for the controller 106 is to maintain the level of measured temperature (inside the tissue) at a desired level during the course of treatment.

According to one embodiment herein, the radio frequency (RF) generator of the system, in communication with the controller/optimizer 106, is configured to receive the value for RF energy, RF frequency, and start and stop time for the treatment and accordingly irradiates the RF radiation. The radio frequency (RF) antenna/transducer 101, in communication with the RF generator, irradiate the RF radiations towards the nerve/disk 107 and the radio frequency (RF) absorber/distributor 102.

Figure 2:
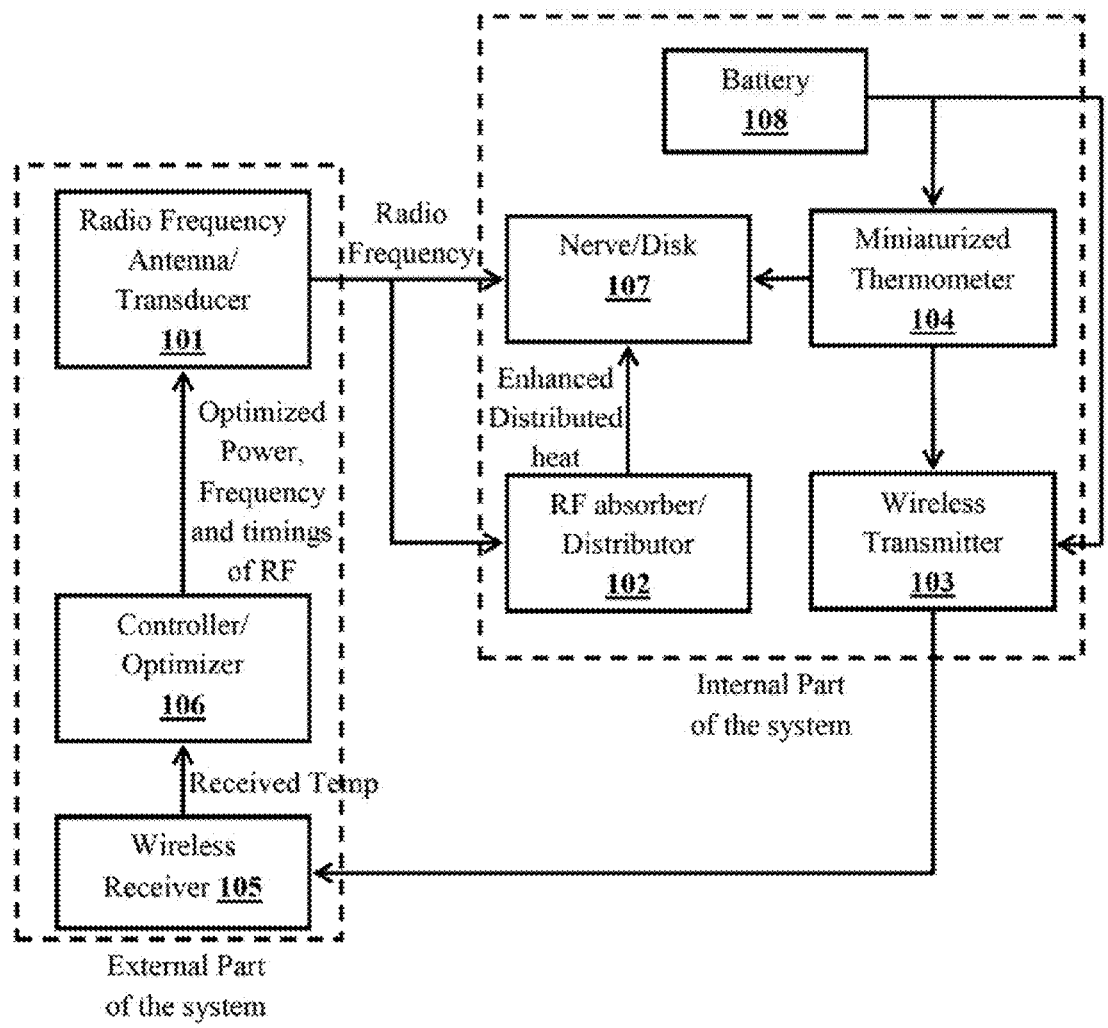
FIG. 2 illustrates a block diagram of the battery powered system for generating heat at the target area of the patient's body, according to an embodiment herein.

FIG. 2 illustrates a block diagram of the system powered by a battery for generating heat at the target area of the patient's body, according to an embodiment herein. The system comprises an internal part/unit/section and an external part/unit/section. The system comprises a plurality of needles/probes/plates/rods, a radio frequency (RF) antenna/transducer 101, a radio frequency (RF) generator, a controller/optimizer 106, a wireless receiver 105, a radio frequency (RF) absorber/distributor 102, a miniaturized thermometer 104, a wireless transmitter 103, and a battery 108. The miniaturized thermometer 104, the radio frequency (RF) absorber/distributor 102, the wireless transmitter 103, the battery 108 and the plurality of needles/probes collectively or integrally form an internal part/unit of the system. The radio frequency (RF) antenna/transducer 101, the controller/optimizer 106 and the wireless receiver 105 collectively form an external part/unit of the system. The internal part/unit of the system is implanted at the target location of the patient's body. The external part/unit of the system is placed outside the patient's body and is under supervision of a physician.

According to one embodiment herein, the system comprises the plurality of needles/probes/plates/rods which are inserted and implanted at the target area in the patient's body. The implanting of needle/probe at the target location eliminates the need to re-insert the needle/probe for plurality of times or several times thereby potentially decreasing the risk of infection, bleeding and the discomfort from the insertion of the needle. The radio frequency radiation generates heat at the tip of a needle or probe. The target area for radio-frequency ablation is typically identified using a decision making process that includes imaging studies, like X-rays, CT scans and MRIs, physical examination of the patient, response to previous treatment modalities, and diagnostic local anesthetic injections, in-order to confirm that the target is actually involved in a pain generating process. Once the target is identified, the wire type probes are inserted percutaneously using a needle under the guidance of fluoroscopy or CT scan. The larger probes and rods are placed surgically under direct vision and secured at the target location.

According to one embodiment herein, the miniaturized thermometer 104 of the system is configured to measure a temperature of a nerve or disk 107 at the target place. The miniaturized thermometer 104 is positioned inside the RF absorber/distributor 102, and the absorber/distributor 102 is placed close to the nerve or disk 107 to be irradiated. The information corresponding to the measured temperature is transmitted over the wireless transmitter 103 to the external part of the system.

According to one embodiment herein, the external part of the system receives the measured temperature information through the wireless receiver 105. The controller/optimizer 106, in communication with the wireless receiver 105, is configured to calculate a suitable value for RF energy and frequency as well as the start/stop time for the treatment. The values are calculated based on the received temperature information. The controller/optimizer 106 is selected from the group consisting of a variety of controllers including but not restricted to a Proportional-integral-Derivative (PID) controller, an Optimal Controller, a Fuzzy Controller, a Neural Controller, a Model-Based Controller and the like. The control criterion for the controller 106 is to maintain the level of measured temperature (inside the tissue) at a desired level during the course of treatment.

According to one embodiment herein, the radio frequency (RF) generator of the system, in communication with the controller/optimizer 106, is configured to receive the value for RF energy, RF frequency, start and stop time for the treatment and accordingly irradiates the RF radiation. The radio frequency (RF) antenna/transducer 101, in communication with the RF generator, irradiate the RF radiations towards the nerve/disk 107 and the radio frequency (RF) absorber/distributor 102.

The miniaturized thermometer 104 and the wireless transmitter 103 are powered by the battery 108. The battery 108 eliminates the need for recharging or powering-up of the miniaturized thermometer 104 and the wireless transmitter 103 using the externally irritated RF power. The battery 108 is recharged from outside by using wireless battery charging techniques whenever necessary.

Figure 3:
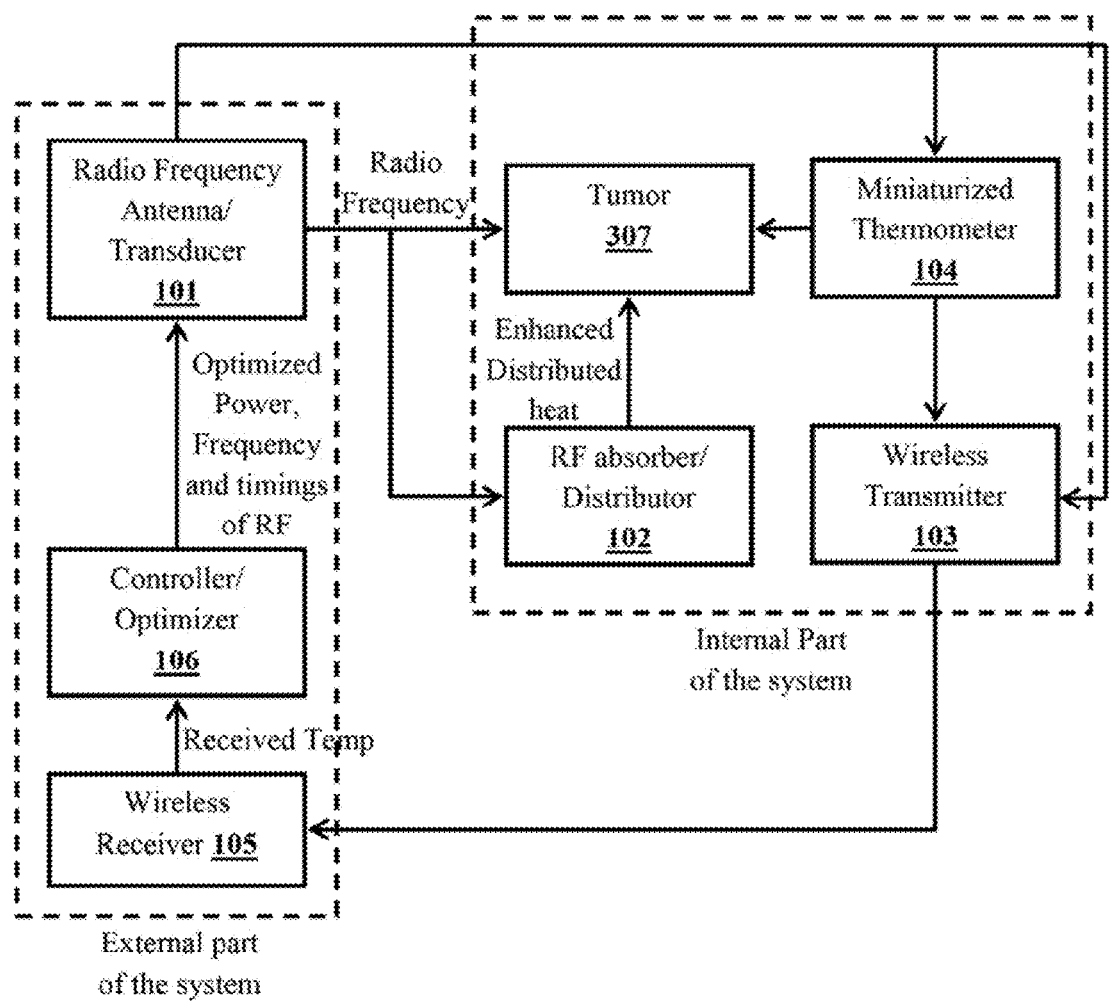
FIG. 3 illustrates a block diagram of the system for generating heat at the tumor of the patient's body, according to an embodiment herein.

FIG. 3 illustrates a block diagram of the system for generating heat at the tumor of the patient's body, according to an embodiment herein. The system comprises an internal part/unit/section and an external part/unit/section. The system comprises a plurality of needles/probes/plates/rods, a radio frequency (RF) antenna/transducer 101, a radio frequency (RF) generator, a controller/optimizer 106, a wireless receiver 105, a radio frequency (RF) absorber/distributor 102, a miniaturized thermometer 104, and a wireless transmitter 103. The miniaturized thermometer 104, the radio frequency (RF) absorber/distributor 102, the wireless transmitter 103 and the plurality of needles/probes collectively or integrally form an internal part/unit of the system. The radio frequency (RF) antenna/transducer 101, the controller/optimizer 106 and the wireless receiver 105 collectively form an external part/unit of the system. The internal part/unit of the system is implanted at the target location of the patient's body. The external part/unit of the system is placed outside the patient's body and is under supervision of a physician.

According to one embodiment herein, the system comprises the plurality of needles/probes plates/rods which are inserted and implanted at the target area in the patient's body. The implanting of needle/probe at the target location eliminates the need to re-insert the needle/probe for plurality of times or several times thereby potentially decreasing the risk of infection, bleeding and the discomfort from the insertion of the needle. The radio frequency radiation generates heat at the tip of a needle or probe. The target area for radio-frequency ablation is typically identified using a decision making process that includes imaging studies, like X-rays, CT scans and MRIs, physical examination of the patient, response to previous treatment modalities, and diagnostic local anesthetic injections, in-order to confirm that the target is actually involved in a pain generating process. Once the target is identified, the wire type probes are inserted percutaneously using a needle under the guidance of fluoroscopy or CT scan. The larger probes and rods are placed surgically under direct vision and secured at the target location.

According to one embodiment herein, the miniaturized thermometer 104 of the system is configured to measure a temperature of the tumor 307 at the target place. The miniaturized thermometer 104 is positioned inside the RF absorber/distributor 102, and the absorber/distributor 102 is placed close to the tumor 307 to be irradiated. The information corresponding to the measured temperature is transmitted over the wireless transmitter 103 to the external part of the system. The miniaturized thermometer 104 and the wireless transmitter 103 operates on a radio frequency (RF) charged battery. The battery uses the RF energy emitted by the RF transducer to recharge itself.

According to one embodiment herein, the external part of the system receives the measured temperature information through the wireless receiver 105. The controller/optimizer 106, in communication with the wireless receiver 105, is configured to calculate a suitable value for RF energy and frequency as well as the start/stop time for the treatment. The values are calculated based on the received temperature information. The controller/optimizer 106 is selected from the group consisting of a variety of controllers including but not restricted to a Proportional-Integral-Derivative (PID) controller, an Optimal Controller, a Fuzzy Controller, a Neural Controller, a Model-Based Controller and the like. The control criterion for the controller 106 is to maintain the level of measured temperature (inside the tissue) at a desired level during the course of treatment.

According to one embodiment herein, the radio frequency (RF) generator of the system, in communication with the controller/optimizer 106, is configured to receive the value for RF energy, RF frequency, and start and stop time for the treatment and accordingly irradiates the RF radiation. The radio frequency (RF) antenna/transducer 101, in communication with the RF generator, irradiate the RF radiations towards the tumor 307 and the radio frequency (RF) absorber/distributor 102.

The major portion of RF is absorbed by the RF absorber/distributer 102 surgically positioned close/attached to the tumor 307, ensuring that the RF energy transmitted from the absorber/distributer 102 to the tumor 307 and converted to heat, damaging the cancer/tumor cells. The miniaturized thermometer 104, also positioned closed/attached to the tumor 307 measures the temperature during the procedure. The measured temperature transmitted via wireless transmitter 103 to the controller 106 outside the patient body is analyzed by the controller/optimizer and the dose/timing of the energy during each treatment as well as planning of the following treatments are optimized based on the measurements.

Figure 4:
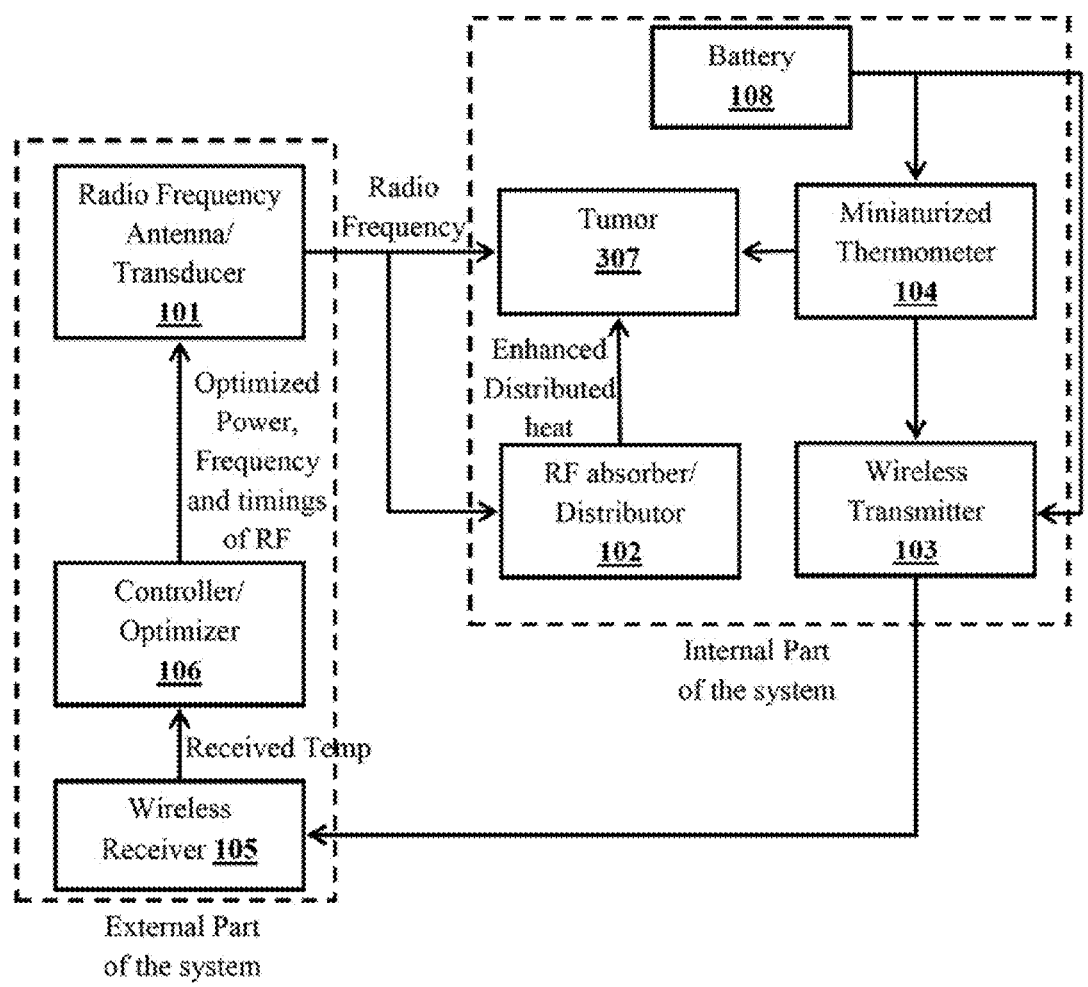
FIG. 4 illustrates a block diagram of the battery powered system for generating heat at the tumor of the patient's body, according to an embodiment herein.

FIG. 4 illustrates a block diagram of the system powered by a battery for generating heat at the tumor of the patient's body, according to an embodiment herein. The system comprises an internal part/unit/section and an external part/unit/section. The system comprises a plurality of needles/probes/plates/rods, a radio frequency (RF) antenna/transducer 101, a radio frequency (RF) generator, a controller/optimizer 106, a wireless receiver 105, a radio frequency (RF) absorber/distributor 102, a miniaturized thermometer 104, a wireless transmitter 103, and a battery 108. The miniaturized thermometer 104, the radio frequency (RF) absorber/distributor 102, the wireless transmitter 103, the battery 108 and the plurality of needles/probes collectively or integrally form an internal part/unit of the system. The radio frequency (RF) antenna/transducer 101, the controller/optimizer 106 and the wireless receiver 105 collectively form an external part/unit of the system. The internal part/unit of the system is implanted at the target location of the patient's body. The external part/unit of the system is placed outside the patient's body and is under supervision of a physician.

According to one embodiment herein, the system comprises the plurality of needles/probes/plates/rods which are inserted and implanted at the target area in the patient's body. The implanting of needle/probe at the target location eliminates the need to re-insert the needle/probe for plurality of times or several times thereby potentially decreasing the risk of infection, bleeding and the discomfort from the insertion of the needle. The radio frequency radiation generates heat at the tip of a needle or probe. The target area for radio-frequency ablation is typically identified using a decision making process that includes imaging studies, like X-rays, CT scans and MRIs, physical examination of the patient, response to previous treatment modalities, and diagnostic local anesthetic injections, in-order to confirm that the target is actually involved in a pain generating process. Once the target is identified, the wire type probes are inserted percutaneously using a needle under the guidance of fluoroscopy or CT scan. The larger probes and rods are placed surgically under direct vision and secured at the target location.

According to one embodiment herein, the miniaturized thermometer 104 of the system is configured to measure a temperature of the tumor 307 at the target place. The miniaturized thermometer 104 is positioned inside the RF absorber/distributor 102, and the absorber/distributor 102 is placed close to the tumor 307 to be irradiated. The information corresponding to the measured temperature is transmitted over the wireless transmitter 103 to the external part of the system.

According to one embodiment herein, the external part of the system receives the measured temperature information through the wireless receiver 105. The controller/optimizer 106, in communication with the wireless receiver 105, is configured to calculate a suitable value for RF energy and frequency as well as the start/stop time for the treatment. The values are calculated based on the received temperature information. The controller/optimizer 106 is selected from the group consisting of a variety of controllers including but not restricted to a Proportional-integral-Derivative (PID) controller, an Optimal Controller, a Fuzzy Controller, a Neural Controller, a Model-Based Controller and the like. The control criterion for the controller 106 is to maintain the level of measured temperature (inside the tissue) at a desired level during the course of treatment.

According to one embodiment herein, the radio frequency (RF) generator of the system, in communication with the controller/optimizer 106, is configured to receive the value for RF energy, RF frequency, and start and stop time for the treatment and accordingly irradiates the RF radiation. The radio frequency (RF) antenna/transducer 101, in communication with the RF generator, irradiate the RF radiations towards the tumor 307 and the radio frequency (RF) absorber/distributor 102.

The miniaturized thermometer 104 and the wireless transmitter 103 are powered by the battery 108. The battery 108 eliminates the need for recharging or powering-up of the miniaturized thermometer 104 and the wireless transmitter 103 using the externally irritated RF power. The battery 108 is recharged from outside by using wireless battery charging techniques whenever necessary.

The major portion of RF is absorbed by the RF absorber/distributor 102 surgically positioned close/attached to the tumor 307, ensuring that the RF energy transmitted from the absorber/distributer 102 to the tumor 307 and converted to heat, damaging the cancer/tumor cells. The miniaturized thermometer 104, also positioned closed/attached to the tumor 307 measures the temperature during the procedure. The measured temperature transmitted via wireless transmitter 103 to the controller 106 outside the patient body is analyzed by the controller/optimizer and the dose/timing of the energy during each treatment as well as planning of the following treatments are optimized based on the measurements.

Figure 5:
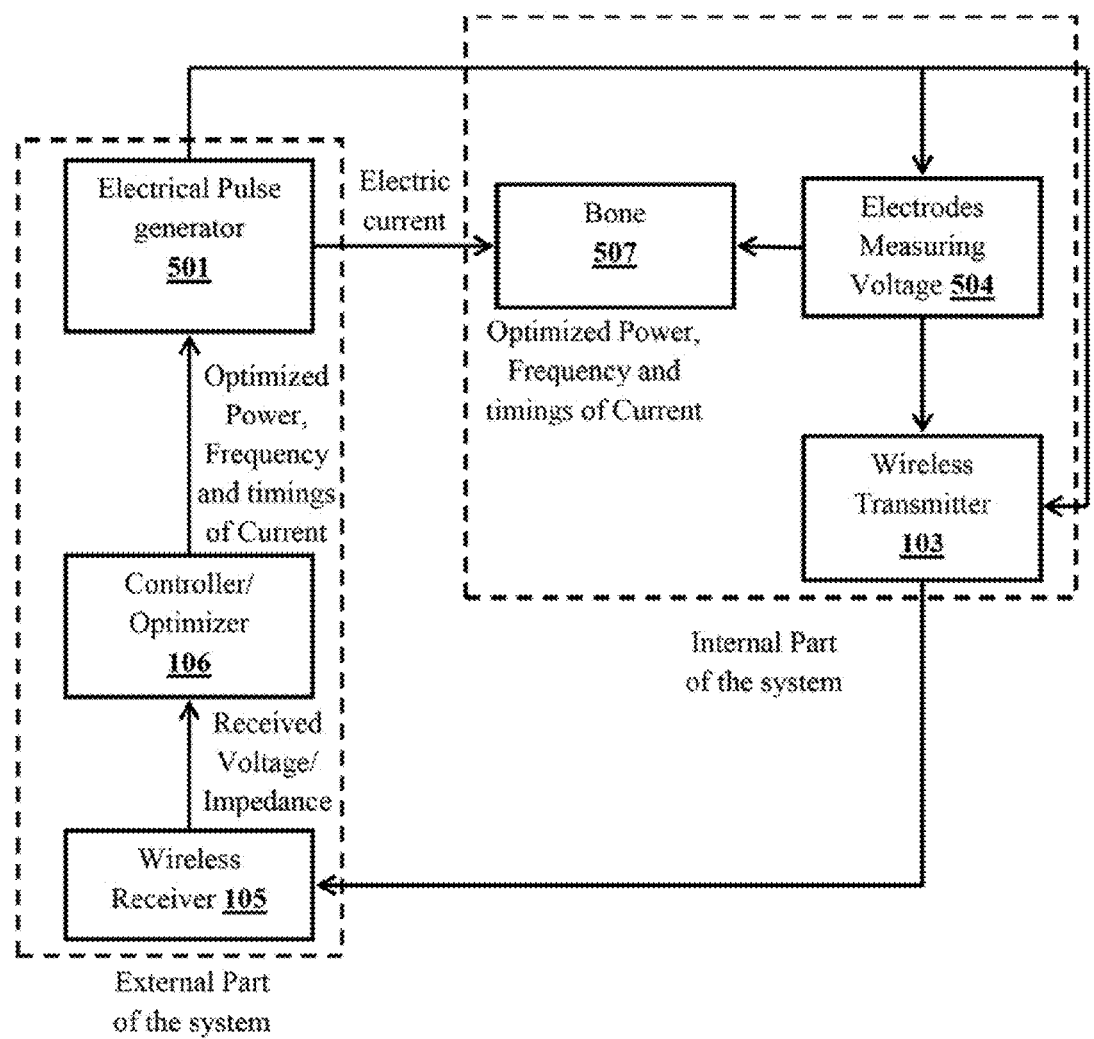
FIG. 5 illustrates a block diagram of the system for generating heat at a bone of the patient's body, according to an embodiment herein.

FIG. 5 illustrates a block diagram of the system for generating heat at the bone of the patient's body, according to an embodiment herein. The system comprises an internal part/unit/section and an external part/unit/section. The system comprises a plurality of needles/probes/plates/rods, an electrical pulse generator 501, a controller/optimizer 106, a wireless receiver 105, an electrode measuring voltage 504, and a wireless transmitter 103. The electrode measuring voltage 504, the wireless transmitter 103 and the plurality of needles/probes collectively or integrally form an internal part/unit of the system. The electrical pulse generator 501, the controller/optimizer 106 and the wireless receiver 105 collectively form an external part/unit of the system. The internal part/unit of the system is implanted at the target location of the patient's body. The external part/unit of the system is placed outside the patient's body and is under supervision of a physician.

According to one embodiment herein, the system comprises the plurality of needles/probes/plates/rods which are inserted and implanted at the target area in the patient's body. The implanting of needle/probe at the target location eliminates the need to re-insert the needle/probe for plurality of times or several times thereby potentially decreasing the risk of infection, bleeding and the discomfort from the insertion of the needle. The radio frequency radiation generates heat at the tip of a needle or probe. The bone for radio-frequency ablation is typically identified using a decision making process that includes imaging studies, like X-rays, CT scans and MRIs, physical examination of the patient, response to previous treatment modalities, and diagnostic local anesthetic injections, in-order to confirm that the target is actually involved in a pain generating process. Once the target is identified, the wire type probes are inserted percutaneously using a needle under the guidance of fluoroscopy or CT scan. The larger probes and rods are placed surgically under direct vision and secured at the target location.

According to one embodiment herein, the electrode measuring voltage 504 of the system is configured to measure a temperature of the bone 507 at the target place. The electrode measuring voltage 504 is positioned inside the RF absorber/distributor, and the absorber/distributor is placed close to the bone 507 to be irradiated. The information corresponding to the measured temperature is transmitted over the wireless transmitter 103 to the external part of the system. The miniaturized thermometer 104 and the wireless transmitter 103 operates on a radio frequency (RF) charged battery. The battery uses the RF energy emitted by the RF transducer to recharge itself.

According to one embodiment herein, the external part of the system receives the measured temperature information through the wireless receiver 105. The controller/optimizer 106, in communication with the wireless receiver 105, is configured to calculate a suitable value for RF energy and frequency as well as the start/stop time for the treatment. The values are calculated based on the received temperature information. The controller/optimizer 106 is selected from the group consisting of a variety of controllers including but not restricted to a Proportional-Integral-Derivative (PID) controller, an Optimal Controller, a Fuzzy Controller, a Neural Controller, a Model-Based Controller and the like. The control criterion for the controller 106 is to maintain the level of measured temperature (inside the tissue) at a desired level during the course of treatment.

According to one embodiment herein, the radio frequency (RF) generator of the system, in communication with the controller/optimizer 106, is configured to receive the value for RF energy, RF frequency, and start and stop time for the treatment and accordingly irradiates the RF radiation. The electrical pulse generator 501, in communication with the RF generator, irradiate the RF radiations towards the bone 507 and the radio frequency (RF) absorber/distributor.

The free-standing device and the form that is part of the hardware, is used for other non-spinal uses, for example hip and knee replacement hard wares. This is helpful with the pain that the patients experience after implanting the hardware and the normal healing phase has lapsed.

The device and concept produce analgesia via one or more of the following mechanisms amongst other mechanisms of action:
1. Heat: By destroying the nerves and other structures
2. It increases circulation to an area thus increase supply of oxygen and nutrients and expedite eliminating carbon dioxide and metabolic waste.
3. By activating nociception locally that acts to activate nervous system pathways and other non-nerve cells and pathways and tissues and produce analgesia.

Figure 6:
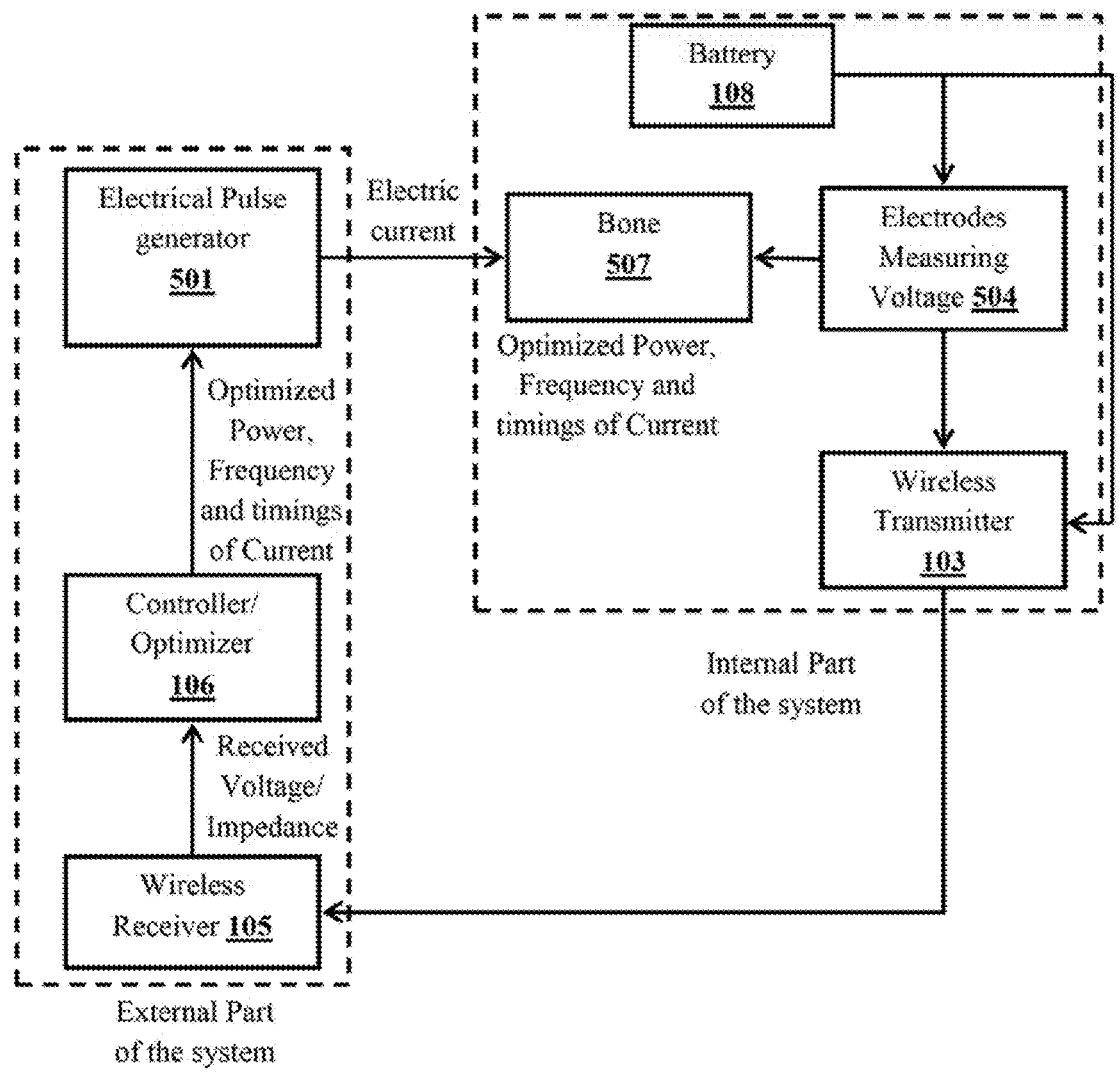
FIG. 6 illustrates a block diagram of the battery powered system for generating heat at the bone of the patient's body, according to an embodiment herein.

FIG. 6 illustrates a block diagram of the system powered by a battery for generating heat at the bone of the patient's body, according to an embodiment herein. The system comprises an internal part/unit/section and an external part/unit/section. The system comprises a plurality of needles/probes/plates/rods, an electrical pulse generator 501, a controller/optimizer 106, a wireless receiver 105, a radio frequency (RF) absorber/distributor, an electrode measuring voltage 504, a wireless transmitter 103, and a battery 108. The electrode measuring voltage 504, the electrical pulse generator 501, the wireless transmitter 103, the battery 108 and the plurality of needles/probes collectively or integrally form an internal part/unit of the system. The electrical pulse generator 501, the controller/optimizer 106 and the wireless receiver 105 collectively form an external part/unit of the system. The internal part/unit of the system is implanted at the target location of the patient's body. The external part/unit of the system is placed outside the patient's body and is under supervision of a physician.

According to one embodiment herein, the system comprises the plurality of needles/probes/plates/rods which are inserted and implanted at the target area in the patient's body. The implanting of needle/probe at the target location eliminates the need to re-insert the needle/probe for plurality of times or several times thereby potentially decreasing the risk of infection, bleeding and the discomfort from the insertion of the needle. The radio frequency radiation generates heat at the tip of a needle or probe. The target area for radio-frequency ablation is typically identified using a decision making process that includes imaging studies, like X-rays, CT scans and MRIs, physical examination of the patient, response to previous treatment modalities, and diagnostic local anesthetic injections, in-order to confirm that the target is actually involved in a pain generating process. Once the target is identified, the wire type probes are inserted percutaneously using a needle under the guidance of fluoroscopy or CT scan. The larger probes and rods are placed surgically under direct vision and secured at the target location.

According to one embodiment herein, the electrode measuring voltage 504 of the system is configured to measure a temperature of the bone 507 at the target place. The electrode measuring voltage 504 is positioned inside the RF absorber/distributor, and the absorber/distributor is placed close to the bone 507 to be irradiated. The information corresponding to the measured temperature is transmitted over the wireless transmitter 103 to the external part of the system.

According to one embodiment herein, the external part of the system receives the measured temperature information through the wireless receiver 105. The controller/optimizer 106, in communication with the wireless receiver 105, is configured to calculate a suitable value for RF energy and frequency as well as the start/stop time for the treatment. The values are calculated based on the received temperature information. The controller/optimizer 106 is selected from the group consisting of a variety of controllers including but not restricted to a Proportional-Integral-Derivative (PID) controller, an Optimal Controller, a Fuzzy Controller, a Neural Controller, a Model-Based Controller and the like. The control criterion for the controller 106 is to maintain the level of measured temperature (inside the tissue) at a desired level during the course of treatment.

According to one embodiment herein, the radio frequency (RF) generator of the system, in communication with the controller/optimizer 106, is configured to receive the value for RF energy, RF frequency, and start and stop time for the treatment and accordingly irradiates the RF radiation. The radio frequency (RF) antenna/transducer 101, in communication with the RF generator, irradiate the RF radiations towards the bone 507 and the radio frequency (RF) absorber/distributor.

The electrode measuring voltage 504 and the wireless transmitter 103 are powered by the battery 108. The battery 108 eliminates the need for recharging or powering-up of the electrode measuring voltage 504 and the wireless transmitter 103 using the externally irritated RF power. The battery 108 is recharged from outside by using wireless battery charging techniques whenever necessary.

Figure 7:
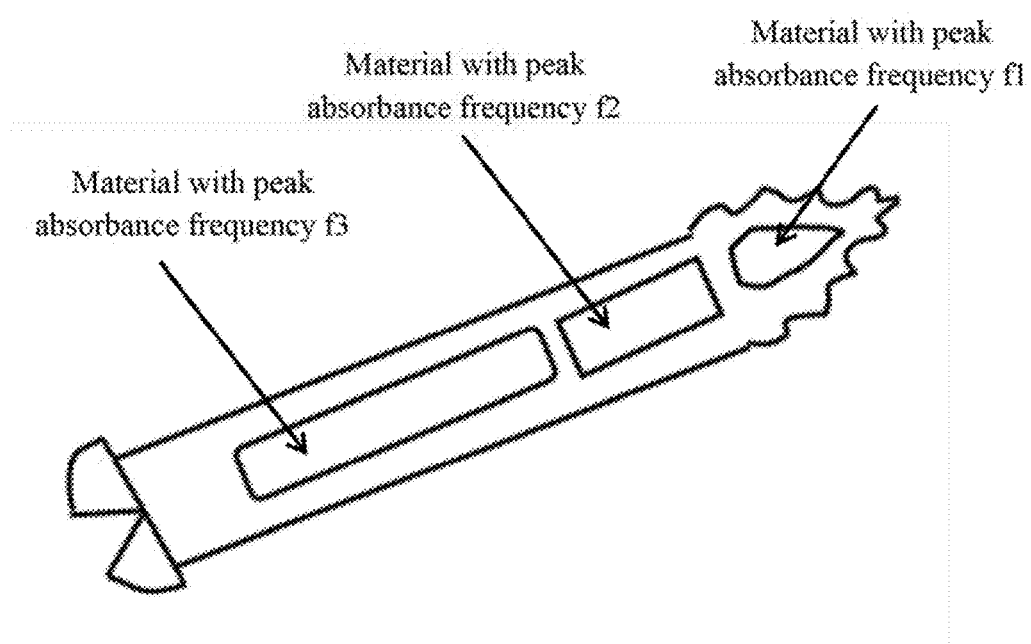
FIG. 7 illustrates a plan view of a screw with a closed loop circuit for heat generators for generating heat from the magnetic field of the RF radiations in the system for generating heat at the target area of the patient's body, according to an embodiment herein.

FIG. 7 illustrates a plan view of a screw with a closed loop circuit for heat generators for generating heat from the magnetic field of the RF radiations in the system for generating heat at the target area of the patient's body, according to an embodiment herein. The miniaturized thermometer 104, the radio frequency (RF) absorber/distributor 102 and the wireless transmitter 103 are placed in the screw. The screw is made of metals having a high rate of radio frequency (RF) absorbability. The radio frequency (RF) absorber/distributor, in communication with the RF antenna/transducer, is configured to convert the magnetic energy of the RF radiations to heat, inside the tissue of the target area and transfer the heat to the disks and/or nerves.

A goal in treatment with RF (in both pain management and tumor suppression) is delivery of different amounts of RF energy to different parts of the tissue being irradiated. Since the irradiated tissues in are mainly the ones in contact or in close vicinity of the absorbers/distributers, the objective translates into delivery of different amount of RF to different implanted absorbers/distributors.

Affinity to absorb RF in different materials (for example, metals/alloys) varies in different RF frequencies. In other words, metal 1 has the maximum level of absorbance at frequency f1 while metal 2 has the maximum level of absorbance at frequency f2, and metal 3 has the maximum level of absorbance at frequency f3. In covering the pedicle screws and other instrumentation with absorbers/distributers, the system covers different parts of the instrumentations with different absorber materials having significantly different maximum peak absorbance RF frequencies so that when the screws are exposed to an RF wave of a specific frequency, only the targeted absorbent and the tissue around it are highly affected by the energy. This capability allows irradiating only the tissue that requires treatment to be irradiated at each treatment session and avoid over-irradiation of all other tissues.

The system is used for both existing spinal hardware that is already implanted in patient's body as well as the new hardware to be implanted in patient's body. For the patients who already have existing hardware, the system hardware along with the algorithmic/software components can be inserted/implanted as a free-standing/separate device through a simple surgical procedure in a clinic or hospital operating room, percutaneously or through a surgical incision. A more recommended and efficient method of implementing the system is to integration of the hardware components (absorbers, thermometer and wireless transmitter) as a component of the spinal instrumentation that are going to be implanted in the patient from the beginning. This integration not only avoids additional surgery but also creates a more effective standard of practice in the field for spinal instrumentation that allows intelligent and targeted RF treatment.

Figure 8A:
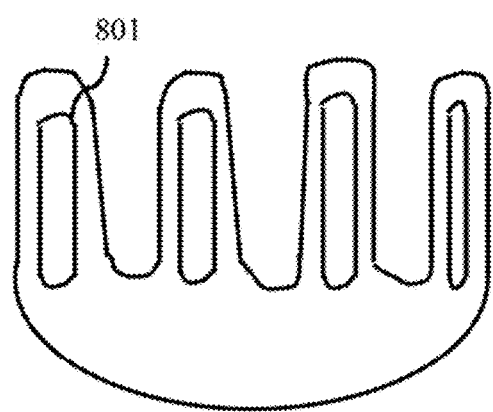
FIG. 8A illustrates a top view of a RF absorber/transducer with a closed loop circuit for electron flow in the system for generating heat at the target area of the patient's body, according to an embodiment herein.
Figure 8B:
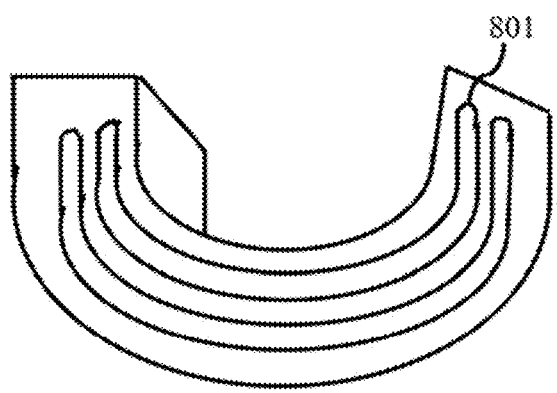
FIG. 8B illustrates a top view of a RF absorber/transducer with a multilayer structure comprising multiple closed loop circuits for generating heat in the system for generating heat at the target area of the patient's body, according to an embodiment herein.

FIG. 8A and FIG. 8B illustrates a structural diagram of a RF absorber/distributor 102 that comprises a plurality of closed loop circuits 801, according to an embodiment of the present disclosure. The plurality of closed loop circuits 801 is configured to perform re-circulation of RF radiation and to amplify the process of conversion of RF energy to heat. The RF absorbers/distributors 102 are made of a metal and/or silicon based material whose rate of absorbing RF is higher than biological tissues. The system is designed to be independent of the material used as distributer/absorber/screws, which enables the system to work with all types of implantable material.

Figure 9:
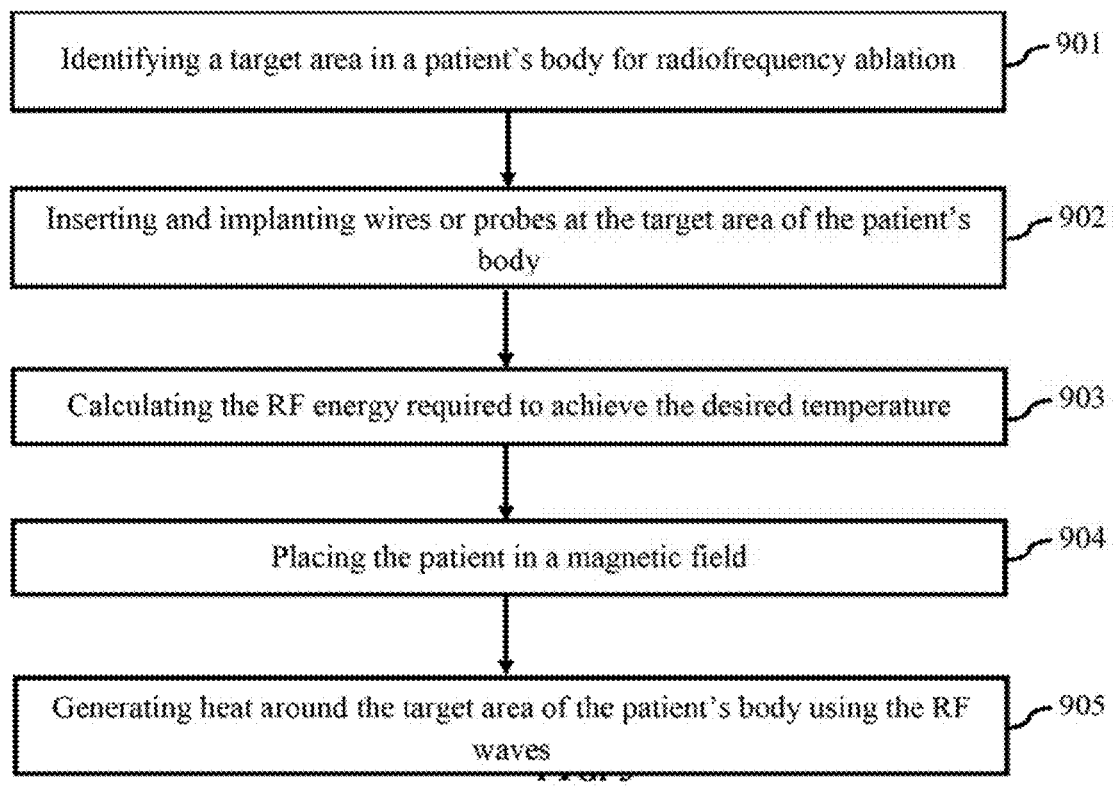
FIG. 9 illustrates a flowchart explaining the process steps in the method for generating heat at a target area of a patient's body, according to an embodiment herein.

The various embodiments herein provide a method for generating heat at a target area of a patient's body. FIG. 9 illustrates a flowchart indicating the steps involved in the method for generating heat at a target area of a patient's body, according to an embodiment of the present disclosure. The method comprises following steps of: A target area is identified in a patient's body for radio-frequency ablation (901). One or more wires or probes or plates or rods are inserted and implanted at the target area of the patient's body (902). The amount of radio frequency (RF) energy required to achieve the desired temperature at the target site is calculated (903). The patient is placed in a magnetic field (904). The heat is generated around the target area of the patient's body utilizing the radio frequency (RF) waves (905). The heat generated destroys the target remotely. The temperature at the target area is monitored remotely, and the monitored temperature information is sent to the physician at regular interval of time.

According to one embodiment herein, the steps for calculating the amount of radio frequency energy required to achieve the desired temperature at the target site comprises: The values of at-least last two measured temperatures are estimated at time "t-1" and "t". One or more fuzzy rules are applied on the estimated temperature values at time "t-1" and "t". The power of the radio frequency (RF) is identified based on the fuzzy rules and the temperature values. Further the frequency and timing of radio frequency (RF) radiation is identified based on the measured temperature.

According to one embodiment of the present invention, the formulation used by the system for calculating the parameters required to achieve the desired temperature at the target site comprises a sensor/controller mechanism that is implemented with highly intuitive systems such as fuzzy controller. Table 1 depicts an example of the fuzzy rules that are defined directly by physicians. The fuzzy rules are further optimized by fuzzy algorithms.

TABLE 1

An example for the fuzzy rules that are defined directly by physicians

| Temp at time t | Temp at time t − 1 | | | | |
| --- | --- | --- | --- | --- | --- |
| | Very Low | Low | Med | High | Very High |
| Very Low | Increase RF Much | Increase RF Much | Maintain RF Level | Decrease RF Some | Decrease RF Much |
| Low | Increase RF Much | Increase RF Much | Maintain RF Level | Maintain RF Level | Decrease RF Some |
| Med | Maintain RF Level | Maintain RF Level | Maintain RF Level | Maintain RF Level | Decrease RF Much |
| High | Maintain RF Level | Maintain RF Level | Maintain RF Level | Decrease RF Some | Decrease RF Much |
| Very High | Decrease RF Some | Decrease RF Some | Decrease RF Some | Decrease RF Much | Decrease RF Much |

Figure 10:
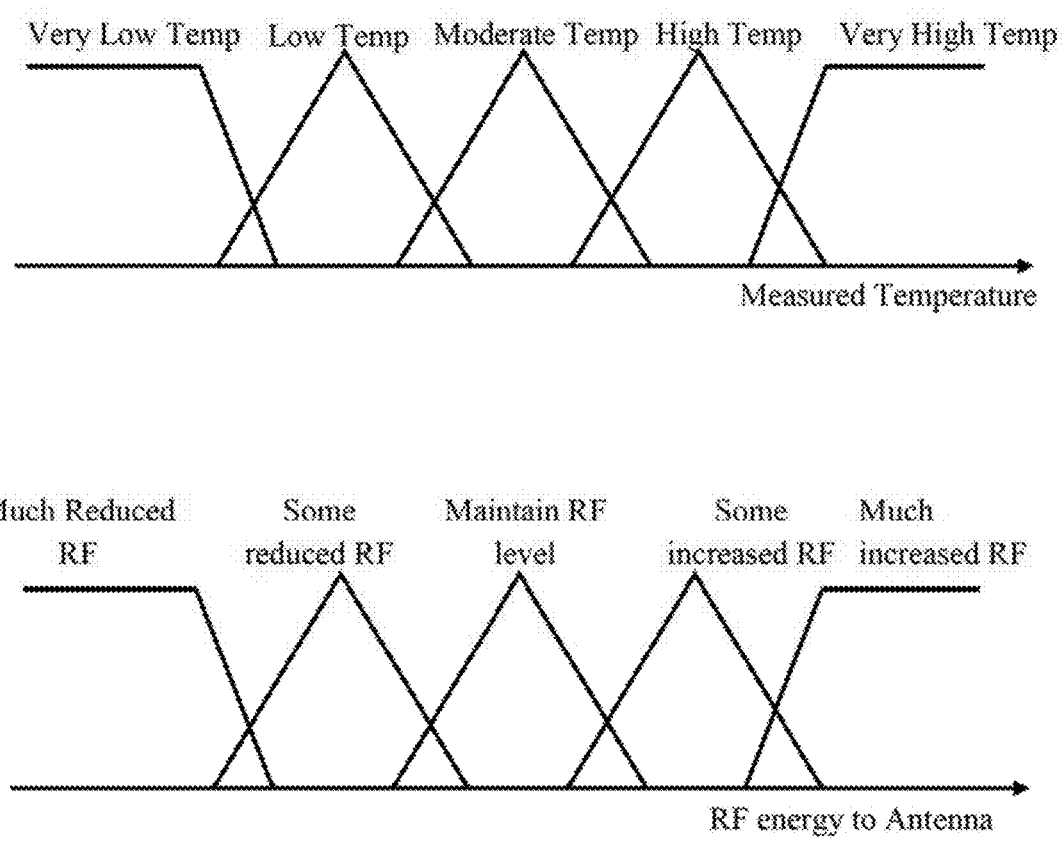
FIG. 10 illustrates a timing chart for the fuzzy sets defining the plurality of fuzzy variables/identifiers, in the method for generating heat at a target area of a patient's body, according to an embodiment herein.

As shown in Table 1, based on the values of the last two measured temperatures (at times "t-1" and "t"), simple fuzzy rules are used to identify the power of the RF. FIG. 10 illustrates fuzzy sets defining various fuzzy variables/identifiers, according to an embodiment of the present disclosure. As shown in FIG. 10, all input and output variables for the controller (in this case temperature and RF energy, respectively) are defined using identifiers such as very low, low, medium, high, very high, and the like. The range of each of these identifiers is initialized and adjusted by the physician. In FIG. 10, triangular membership function is employed to create fuzzy sets but other functions such as trapezoidal and Gaussian are also used for the purpose as well. The physician supervises the controller and easily adjust/revise the function of the controller by changing the values in Table 1 and/or membership functions/sets in FIG. 10. The same type of controller identifies the frequency and timing of RF based on measured temperature.

The foregoing description of the specific embodiments herein will so fully reveal the general nature of the embodiments herein that others can, by applying current knowledge, readily modify and/or adapt for various applications such specific embodiments herein without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the embodiments herein with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A system for generating heat at a target area of a patient's body comprising:
   a radio frequency (RF) antenna or transducer;
   a radio frequency (RF) generator for generating radio frequency (RF) waves, and wherein the radio frequency (RF) generator transmits the generated radio frequency (RF) waves to the radio frequency (RF) antenna or transducer;
   a controller or optimizer for controlling frequency of the radio frequency (RF) waves to be transmitted by the radio frequency (RF) antenna or transducer and a transmission timing, and wherein the transmission timing comprises a start time and a stop time of the transmission of the radio frequency (RF) waves;
   a radio frequency (RF) absorber or distributor, wherein the radio frequency (RF) absorber comprises a plurality of closed loop circuits; and
   a miniaturized thermometer, wherein the miniaturized thermometer is positioned inside the radio frequency absorber or distributer, and wherein the miniaturized thermometer is adapted to be positioned close to the target area of the patient's body, and wherein the miniaturized thermometer measures a temperature of the target area of the patient's body and transmit a measured temperature value to a wireless transmitter, and wherein the wireless transmitter transmits the measured temperature value to a wireless receiver and wherein the miniature thermometer is a temperature sensor.

2. The system according to claim 1, wherein the radio frequency (RF) antenna or transducer, the controller or optimizer and the wireless receiver collectively form an external part of the system.

3. The system according to claim 1, wherein the miniaturized thermometer, the radio frequency (RF) absorber or distributor and the wireless transmitter collectively form an internal part of the system, and wherein the miniaturized thermometer, the radio frequency (RF) absorber or distributor and the wireless transmitter are placed in a screw, and wherein the radio frequency (RF) absorber or distributor is made of metal or silicon based material whose rate of absorbing radio frequency (RF) is higher than that of biological tissues.

4. The system according to claim 1, wherein the wireless transmitter is configured to transmit the measured temperature value received from the miniaturized thermometer to the wireless receiver, and wherein the wireless receiver is placed outside the patient's body.

5. The system according to claim 1, wherein the wireless receiver is configured to transmit the received temperature value to the controller or optimizer.

6. The system according to claim 1, wherein the controller or optimizer calculates a preferred value for RF energy, RF frequency, start and stop time for the treatment, and wherein the values are calculated based on the received temperature value.

7. The system according to claim 1, wherein the controller or optimizer is any of a controller or optimizer selected from a group consisting of a Proportional-Integral-Derivative (PID) controller, an Optimal Controller, a Fuzzy Controller, a Neural Controller and a Model-Based Controller.

8. The system according to claim 1, wherein the controller or optimizer is further configured to maintain the level of measured temperature inside the tissue at a desired level during a course of treatment.

9. The system according to claim 1, wherein the radio frequency (RF) antenna or transducer is configured to receive the value for RF energy, RF frequency, and start and stop time for the treatment, and wherein the radio frequency (RF) generator is configured to irradiate RF energy towards the target area of the patient's body and the radio frequency (RF) absorber or distributor.

10. The system according to claim 1, wherein the radio frequency (RF) absorber or distributor provides re-circulation of radio frequency (RF) energy, and wherein the radio frequency (RF) absorber or distributor is configured to generate heat from magnetic energy of radio frequency (RF), and wherein the radio frequency (RF) absorber or distributor is further configured to distribute generated heat to the target area of the patient's body.

11. The system according to claim 1, wherein the screws or the absorbers or the distributors convert the magnetic energy to heat inside the tissue and transfer the heat to the target area of the patient's body.

12. The system according to claim 1, wherein the target area of the patient's body is selected from a group consisting of disks, nerves, bones, and tumor tissues.

13. The system according to claim 1, further comprises a battery implanted inside the patient's body to supply electrical power to the temperature sensor and the wireless transmitter.

14. The system according to claim 1, further comprises an ultrasonic generator or ultrasonic transducer to generate energy for producing a lesion or heat to induce analgesia in the target area of the patient's body.

15. A method for generating heat at a target area of a patient's body, the method comprises steps of:
   identifying a target area in a patient's body for radiofrequency ablation;
   inserting and implanting one or more wires or probes or plates or rods at the target area of the patient's body;
   calculating an amount of radio frequency (RF) energy required to achieve a desired temperature at the target area of the patient's body;
   placing the patient in a magnetic field; and
   generating a heat around the target area of the patient's body utilizing the radio frequency (RF) waves, and wherein the heat generated destroys the target area remotely, and wherein a temperature at the target area is monitored remotely, and wherein the monitored temperature information is sent to the physician at regular intervals of time;
   wherein the step of calculating the amount of radio frequency energy required to achieve the desired temperature at the target site comprises steps of:
   estimating values of at-least last two measured temperatures at time "t-1" and "t";
   applying one or more fuzzy rules on the estimated temperature values at time "t-1" and "t";
   identifying the power of the radio frequency (RF) based on the fuzzy rules and the temperature values; and
   identifying the frequency and timing of radio frequency (RF) based on the measured temperature.

16. The method according to claim 15, wherein the identification of the target area in the patient's body for radiofrequency ablation is done through one or more imaging technologies selected from a group consisting of X-rays, CT scans, MRIs, and physical examination of the patient, response to previous treatment modalities, and diagnostic local anesthetic injections, and wherein the probe is inserted when the target area is identified, and wherein the probe is inserted percutaneously using a needle under the guidance of fluoroscopy or CT scan, and wherein larger probes and rods are inserted surgically under direct vision and secured at the target area in the patient's body.

17. The method according to claim 15, wherein the target area of the patient's body is selected from a group consisting of disks, nerves, bones, and tumor tissues.

18. The method according to claim 15, further comprises a real time monitoring of the heat generated and the temperature of the tissue.

19. The method according to claim 15, further comprises implanting a battery inside the patient's body to supply electrical power to the temperature sensor and the wireless transmitter.

20. The method according to claim 15, wherein an ultrasonic generator or ultrasonic transducer is employed to generate energy for producing a lesion or heat to induce analgesia in the target area of the patient's body.

* * * * *